(12) United States Patent
Shokanov

(10) Patent No.: US 12,025,001 B2
(45) Date of Patent: Jul. 2, 2024

(54) METHOD OF USING A DISSOLVABLE DEPLOYMENT DEVICE FOR THE TRANSFER OF ULTRAHIGH RESOLUTION NANOPARTICLE TRACER ADDITIVES INTO A WELLBORE

(71) Applicant: Talgat Shokanov, Houston, TX (US)

(72) Inventor: Talgat Shokanov, Houston, TX (US)

( * ) Notice: Subject to any disclaimer, the term of this patent is extended or adjusted under 35 U.S.C. 154(b) by 9 days.

(21) Appl. No.: 17/945,889

(22) Filed: Sep. 15, 2022

(65) Prior Publication Data

US 2024/0093603 A1    Mar. 21, 2024

(51) Int. Cl.
*E21B 49/08* (2006.01)
*C09K 8/92* (2006.01)
*G01N 23/223* (2006.01)
*G01N 33/28* (2006.01)

(52) U.S. Cl.
CPC .............. *E21B 49/08* (2013.01); *C09K 8/92* (2013.01); *G01N 23/223* (2013.01); *G01N 33/2823* (2013.01); *G01N 33/2835* (2013.01); *C09K 2208/10* (2013.01); *E21B 2200/08* (2020.05); *G01N 2223/076* (2013.01); *G01N 2223/507* (2013.01); *G01N 2223/637* (2013.01)

(58) Field of Classification Search
CPC ........ E21B 47/11; E21B 43/267; E21B 43/26; E21B 49/088; E21B 49/08
See application file for complete search history.

(56) References Cited

U.S. PATENT DOCUMENTS 11,808,102 B1 * 11/2023 Roberts ................... E21B 47/00

* cited by examiner

*Primary Examiner* — Zakiya W Bates
(74) *Attorney, Agent, or Firm* — Kearney, McWilliams & Davis, PLLC; John M. DeBoer

(57) ABSTRACT

A method of using a tracer additive in a wellbore that includes using a deployment device, the device configured with a hollowed region, and disposing a tracer additive into the hollowed region. The method includes sending the deployment device into the wellbore in manner whereby the deployment device arrives at a desired location, and sufficiently dissolving the deployment device so that the tracer additive comes into contact with a target formation fluid. The tracer additive has a first composition, and is in a solid powder form.

20 Claims, 7 Drawing Sheets

METHOD OF USING A DISSOLVABLE DEPLOYMENT DEVICE FOR THE TRANSFER OF ULTRAHIGH RESOLUTION NANOPARTICLE TRACER ADDITIVES INTO A WELLBORE

BACKGROUND

Field of the Disclosure

This disclosure generally relates to the use of an innovative type of chemical additive known as a 'tracer' in a wellbore or other comparable subterranean formation. The tracer may be disposed into a dissolvable device, and then transferred into the wellbore. The tracer may be flown out from the targeted structure with a resultant produced fluid, then tested in a manner that facilitates determination of flow performance, or a model of one or more production parameters associated with the wellbore. The disclosure relates to using ultrahigh resolution inert nano particle tracer technology in oil, gas and geothermal wells that need not necessarily be hydraulicly fractured.

Background of the Disclosure

A hydrocarbon-based economy continues to be dominant force in the modern world. As such, locating and producing hydrocarbons, along with understanding the flow performance of subsurface formations, continues to demand attention from the oil and gas (O&G) industry. A well or wellbore is generally drilled in order to recover valuable hydrocarbons and other desirable materials trapped in geological formations in the Earth, which are later refined into commercial products, such as gasoline or natural gas.

Once the drilling is finished, a production string is typically placed all the way into the wellbore. To gain access to hydrocarbons, selected portions of the production string (and formation) are often perforated. Common today to increase or enhance production in the tight or unconventional reservoirs is the use of hydraulic fracturing (i.e., "fracing") in the surrounding formations.

Fracing entails the pumping of fracturing fluids with sand into a formation in an open-hole or via perforations in a cased wellbore or other openings in the casing to form a fracture(s) in the formation. Fracing routinely requires very high fluid pressure and pumping rate and can occur in a multi-stage fracing manner.

The modern design of shale well with multi-stage hydraulic fracturing operations involve pumping from 20 to 100 fracing stages with a cumulative volume of 5 to 20 million gallons of water and from 5 to 20 million pounds of sand per well. This represents the total cost ranging from 4.0 million to 9.5 million U.S. dollars per well. Fracing operations are expensive, increasingly environmentally challenging and emissions intensive, and can represent up to 70% of the total cost for each well.

With such extensive costs, there may be situations where a wellbore is not subjected to hydraulic fracturing, but yet it still might be desirous to have some amount of diagnostic information about the well. For example, producers may desire to know when production occurs from a target formation, such as the bottom/toe end portion of a wellbore. For the sake of flow assurance, it might be desirous to have diagnostic information that may be decoupled from fracturing. It follows that it might be desirous to have diagnostic information about (a part of) the wellbore, but not necessarily a fractured area.

Production diagnostic tools may be used in order to predict well performance, improve well design, or aid in future well development. Typically, diagnostic or surveillance tools include fiber, PLT (production logging), fiber-optic, and liquid chemical tracers.

Use of fiber optic systems that include distributed acoustic sensing (DAS) and distributed temperature surveys (DTS) is known to provide high-end diagnostic results. However, fiber is known to be excessive in cost and deployment complexities, and the time to obtain useful data may be in the realm of weeks or longer. Depending on the complexity, the installation of fiber optic DAS and DTS systems can add as much as $1 million/well to the completed total costs.

PLT also has its favored uses and is a historically well accepted approach, but while perhaps slightly lower in cost, it is known to provide a short snapshot view and information compared to fiber and requires well shut-in and costly wireline intervention.

Conventional chemical liquid tracers have enjoyed success but are also known to have limitations. These tracers are dissolvable in oil and water phases, and typically have fluorescent properties, DNA and ionic, organic materials, or radioactive diagnostic isotopes. Such tracers are used to evaluate fracturing performance, ostensibly to control the effectiveness of multi-stage hydraulic fracturing stimulation. Owing to obvious environmental deficiencies, tracers incorporating radioactive isotopes have largely fallen out of favor. Given their soluble characteristics, conventional chemical tracers must be tailored for individual fluid types, thereby requiring more, and often exotic, formulations for a single stage, increasing the chemical tracer costs appreciably.

Each of the aforementioned techniques: fiber, PLT, and liquid chemical tracer tools also have temperature limitations (i.e., for use in <500° F.) that make their use problematic at best in unconventional or igneous geothermal reservoirs, where temperatures may be as high as 1,000° F. Moreover, these techniques are routinely coupled with the frac operation, and usually used for stages.

The industry needs a simplistic, low-cost diagnostic method that can be used for assessing reservoir quality, completion design, and other wellbore performance parameters, especially for target areas of the formation (such as the wellbore bottom or toe) that need not be related to a particular 'stage'.

The need for an ultrahigh resolution nanoparticle tracer that is versatile, affordable, highly accurate, non-radioactive, non-intrusive and quick to test is increasing as never before for all applications. Thus, there is an urgent need to have accurate, affordable, timely data on wellbore performance or other information. What is needed is a new and improved way of forming and using a fast, cost-favorable, effective, and reliable way of evaluating a wellbore that can be decoupled from a fracturing operation.

SUMMARY

Embodiments of the disclosure pertain to a method of using a tracer additive in a wellbore that may include one or more steps described herein. The method may include using a deployment device, the deployment device configured with a hollowed region. There may be a tracer additive into the hollowed region.

The method may include sending the deployment device into the wellbore in manner whereby the deployment device arrives at a target depth of a formation, which may be in communication with the wellbore. In aspects, the tracer additive in the hollowed region may be initially isolated from contacting the target formation.

The method may include sufficiently dissolving (or letting dissolve) the deployment device so that the tracer additive may be able to come into contact with the target formation and/or respective formation fluid. Upon contact with the target formation fluid for an amount of time, the method may include returning a remnant fluid that includes at least a portion of the tracer additive to a surface.

The target formation and respective fluid may be part of a geothermal well, vertical well, horizontal drilled well, or combinations thereof. In aspects, the remnant fluid may be used in an energy generation process. For example, a fluid may be injected into the geothermal well, energy (such as heat) added thereto, and then the fluid is produced to the surface, where the added energy may be converted in the energy generation process.

An amount of elapsed time to accomplish the step of sufficiently dissolving the deployment device may be in a range of at least 36 hours to no more than 240 hours. Other times of dissolving may be possible. In this respect, the sufficiently dissolving may be passive in that no other human interaction is necessary to accomplish the step.

In aspects, the tracer additive may have a first tracer composition. The tracer additive may be in a solid powder form having an average particle diameter of at least 0.01 μm to no more than 10 μm. The tracer additive may have an average bulk specific gravity, such as in a range of at least 0.6 g/cm$^3$ to no more than 1.6 g/cm3.

There may be instances where the wellbore (or surrounding formation) has certain geological parameters, for example, the wellbore may be associated with a formation temperature of at least 200° F. to no more than 1,000° F. The wellbore may be a vertical wellbore, whereby the sending the deployment device into the wellbore step does not use pump down. The wellbore may include a horizontal portion. As such, the sending the deployment device into the wellbore step may utilize pump down.

The method may include other steps, such as any of: taking a sample of the remnant fluid; testing the sample in order to analyze the remnant fluid in order to provide a set of fluid data; and/or integrating the set of fluid data with other wellbore data in order to determine a parameter associated with performance of the wellbore.

In some aspects, the deployment device may have a desired shape, such as being a spherical member configured to be separated into at least two sections. The deployment device may have an effective outer diameter in a size range of at least 2 inches to no more than 5 inches. Other shapes or sizes may be possible. For example, an OD of 2.5 inches, 3.5 inches, 4.5 inches, and so forth.

The method may include sending a second deployment device carrying a second tracer additive into the wellbore. Upon sufficient dissolving of the second deployment device, the second tracer additive may come into contact with one or more of the target formation fluid, another target formation fluid proximate to the wellbore, or combinations thereof.

The second tracer additive may have a different composition from the tracer additive. The second tracer additive may be in powder form. The second tracer additive may have an average particle diameter, such as of at least 0.01 μm to no more than 10 μm. The second tracer additive may have an average bulk specific gravity, such as of at least 0.6 g/cm$^3$ to no more than 1.6 g/cm3.

In aspects, the testing the sample step may include using a fluorescence response-based analysis. For example, the fluorescence response-based analysis may include use of EDXRF.

Yet other embodiments of the disclosure pertain to a method of using a tracer additive in a wellbore that may include one or more steps of: using a deployment device, the deployment device configured with a hollowed region; disposing a tracer additive into the hollowed region; sending the deployment device into the wellbore in manner whereby the deployment device arrives at a target formation in communication with the wellbore, whereby the tracer additive in the hollowed region is initially isolated from contacting the target formation; sufficiently dissolving the deployment device so that the tracer additive comes into contact with the target formation. The tracer additive may be in a solid powder and has a first tracer composition.

These and other embodiments, features and advantages will be apparent in the following detailed description and drawings.

BRIEF DESCRIPTION OF THE DRAWINGS

A full understanding of embodiments disclosed herein is obtained from the detailed description of the disclosure presented herein below, and the accompanying drawings, which are given by way of illustration only and are not intended to be limitative of the present embodiments, and wherein.

DETAILED DESCRIPTION

Figure 1A:
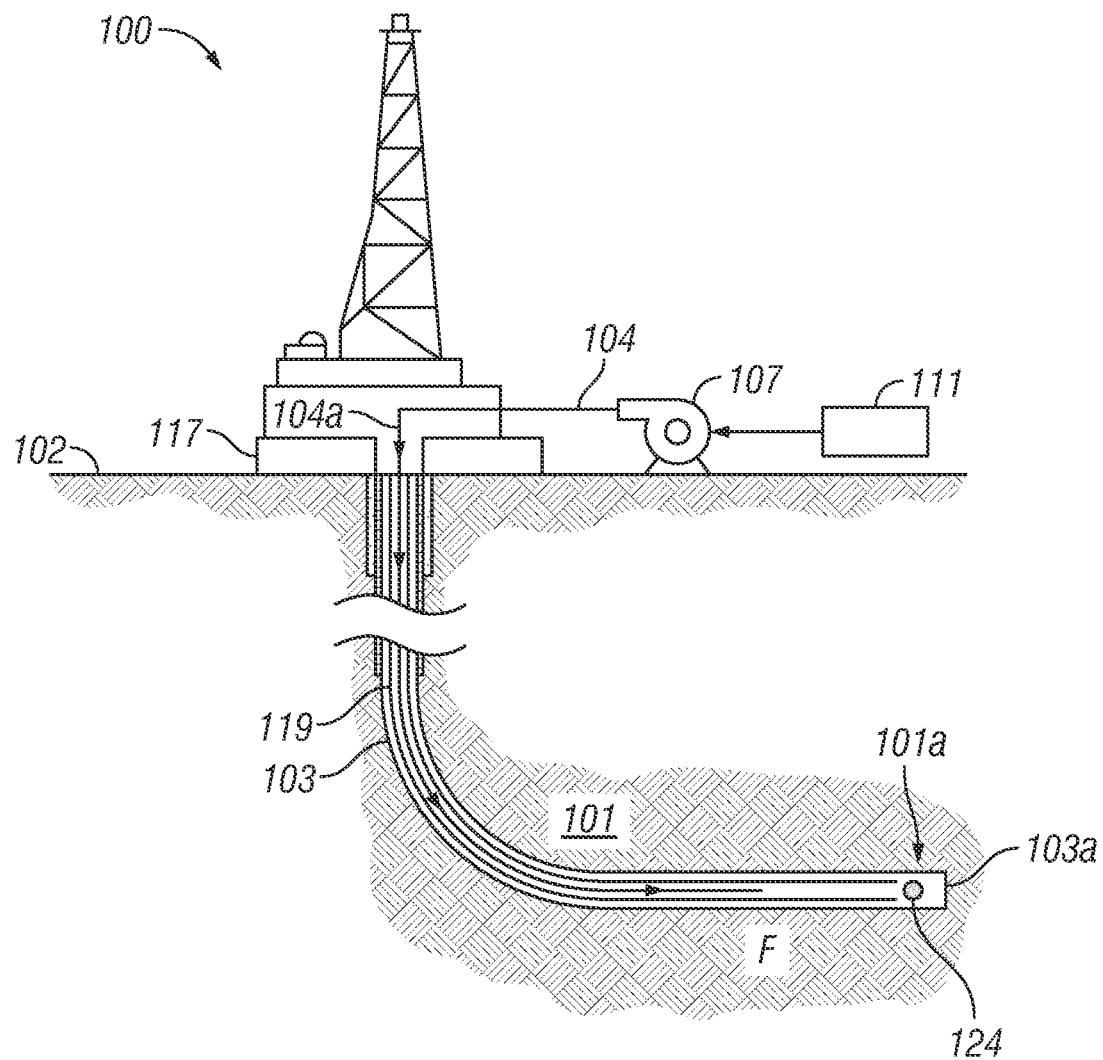
FIG. 1A shows a side view of a system for using a deployment device for the transfer of a tracer additive into a wellbore according to embodiments of the disclosure.

Regardless of whether presently claimed herein or in another application related to or from this application, herein disclosed are novel apparatuses, units, systems, and methods that pertain to use of solid inert tracer additives, details of which are described herein. Embodiments of the disclosure may refer to "in-wellbore tracer deployment"—where the tracer is already in the wellbore (in a deployment device) before deployment of the tracer into the wellbore occurs.

Embodiments of the present disclosure are described in detail with reference to the accompanying Figures. In the following discussion and in the claims, the terms "including" and "comprising" are used in an open-ended fashion, such as to mean, for example, "including, but not limited to . . . ". While the disclosure may be described with reference to relevant apparatuses, systems, and methods, it should be understood that the disclosure is not limited to the specific embodiments shown or described. Rather, one skilled in the art will appreciate that a variety of configurations may be implemented in accordance with embodiments herein.

Although not necessary, like elements in the various figures may be denoted by like reference numerals for consistency and ease of understanding. Numerous specific details are set forth in order to provide a more thorough understanding of the disclosure; however, it will be apparent to one of ordinary skill in the art that the embodiments disclosed herein may be practiced without these specific details. In other instances, well-known features have not been described in detail to avoid unnecessarily complicating the description. Directional terms, such as "above," "below," "upper," "lower," "front," "back," etc., are used for convenience and to refer to general direction and/or orientation, and are only intended for illustrative purposes only, and not to limit the disclosure.

Connection(s), couplings, or other forms of contact between parts, components, and so forth may include conventional items, such as lubricant, additional sealing materials, such as a gasket between flanges, PTFE between threads, and the like. The make and manufacture of any particular component, subcomponent, etc., may be as would be apparent to one of skill in the art, such as molding, forming, press extrusion, machining, or additive manufacturing. Embodiments of the disclosure provide for one or more components to be new, used, and/or retrofitted to existing machines and systems.

Various equipment may be in fluid communication directly or indirectly with other equipment. Fluid communication may occur via one or more transfer lines and respective connectors, couplings, valving, piping, and so forth. Fluid movers, such as pumps, may be utilized as would be apparent to one of skill in the art.

Numerical ranges in this disclosure may be approximate, and thus may include values outside of the range unless otherwise indicated. Numerical ranges include all values from and including the expressed lower and the upper values, in increments of smaller units. As an example, if a compositional, physical or other property, such as, for example, molecular weight, viscosity, melt index, etc., is from 100 to 1,000. it is intended that all individual values, such as 100, 101, 102, etc., and sub ranges, such as 100 to 144, 155 to 170, 197 to 200, etc., are expressly enumerated. It is intended that decimals or fractions thereof be included. For ranges containing values which are less than one or containing fractional numbers greater than one (e.g., 1.1, 1.5, etc.), smaller units may be considered to be 0.0001, 0.001, 0.01, 0.1, etc. as appropriate. These are only examples of what is specifically intended, and all possible combinations of numerical values between the lowest value and the highest value enumerated, are to be considered to be expressly stated in this disclosure. Numerical ranges are provided within this disclosure for, among other things, the relative amount of reactants, surfactants, catalysts, etc. by itself or in a mixture or mass, and various temperature and other process parameters.

Terms

The term "connected" as used herein may refer to a connection between a respective component (or subcomponent) and another component (or another subcomponent), which can be fixed, movable, direct, indirect, and analogous to engaged, coupled, disposed, etc., and can be by screw, nut/bolt, weld, and so forth. Any use of any form of the terms "connect", "engage", "couple", "attach", "mount", etc. or any other term describing an interaction between elements is not meant to limit the interaction to direct interaction between the elements and may also include indirect interaction between the elements described.

The term "fluid" as used herein may refer to a liquid, gas, slurry, single phase, multi phase, pure, impure, etc. and is not limited to any particular type of fluid such as hydrocarbons.

The term "utility fluid" as used herein may refer to a fluid used in connection with any fluid disposed into a wellbore (akin to an injection fluid). The utility fluid may be pressurized, and may be used to carry an additive into the wellbore. 'Utility fluid' may also be referred to and interchangeable with 'service fluid' or comparable.

The term "fluid connection", "fluid communication," "fluidly communicable," and the like, as used herein may refer to two or more components, systems, etc. being coupled whereby fluid from one may flow or otherwise be transferrable to the other. The coupling may be direct, indirect, selective, alternative, and so forth. For example, valves, flow meters, pumps, mixing tanks, holding tanks, tubulars, separation systems, and the like may be disposed between two or more components that are in fluid communication.

The term "pipe", "conduit", "line", "tubular", or the like as used herein may refer to any fluid transmission means, and may be tubular in nature.

The term "tubestring" or the like (such as 'workstring') as used herein may refer to a tubular (or other shape) that may be run into a wellbore. The tubestring may be casing, a liner, production tubing, combinations, and so forth. The tubestring may be multiple pipes (and the like) coupled together. The tubestring may be used for transfer of fluids, or used with some other kind of action, such as drilling, running a tool, or any other kind of downhole action, and combinations thereof.

The term "composition" or "composition of matter" as used herein may refer to one or more ingredients, components, constituents, etc. that make up a material (or material of construction). Composition may refer to a flow stream of one or more chemical components.

The term "chemical" as used herein may analogously mean or be interchangeable to material, chemical material, ingredient, component, chemical component, element, substance, compound, chemical compound, molecule(s), constituent, and so forth and vice versa. Any 'chemical' discussed in the present disclosure need not refer to a 100% pure chemical. For example, although 'water' may be thought of as H2O, one of skill would appreciate various ions, salts, minerals, impurities, and other substances (including at the ppb level) may be present in 'water'. A chemical may include all isomeric forms and vice versa (for example, "hexane", includes all isomers of hexane individually or collectively).

The term "reactive material" as used herein may refer a material with a composition of matter having properties and/or characteristics that result in the material responding to a change over time and/or under certain conditions. The term reactive material may encompass degradable, dissolvable, disassociatable, dissociable, and so on.

The term "dissolvable material" may be analogous to degradable material. The term as used herein may refer to a composition of matter having properties and/or characteristics that, while subject to change over time and/or under certain conditions, lead to a change in the integrity of the material, including to the point of degrading, or partial or complete dissolution. As one example, the material may initially be hard, rigid, and strong at ambient or surface conditions, but over time (such as within about 12-60 hours) and under certain conditions (such as wellbore conditions), the material softens. As another example, the material may initially be hard, rigid, and strong at ambient or surface conditions, but over time (such as within about 12-240 hours) and under certain conditions (such as wellbore conditions), the material dissolves at least partially, and may dissolve completely. The material may dissolve via one or more mechanisms, such as oxidation, reduction, deterioration, go into solution, or otherwise lose sufficient mass and structural integrity.

The term "water" as used herein may refer to a pure, substantially pure, and impure water-based stream, and may include wastewater, process water, fresh water, seawater, produced water, slop water, treated variations thereof, mixes thereof, etc., and may further include impurities, dissolved solids, ions, salts, minerals, and so forth. Water for a frac fluid can also be referred to as 'frac water'.

The term "impurity" as used herein may refer to an undesired component, contaminant, etc. of a composition. For example, a mineral or an organic compound may be an impurity of a water stream.

The term "frac fluid" as used herein may refer to a fluid injected into a well as part of a frac operation. Frac fluid is often characterized as being largely water, but with other constituents such as proppant, friction reducers, and other additives or compounds.

The term "produced fluid", "production fluid", and the like as used herein may refer to water, gas, mixtures, and the like recovered from a subterranean formation or other area near the wellbore. Produced fluid may include hydrocarbons or aqueous, such as flowback water, brine, salt water, or formation water. Produced water may include water having dissolved and/or free organic materials. Produced fluid may be akin to 'wellbore fluid', in that the fluid may be returned from the wellbore. Produced fluid may include utility fluids and formation fluids.

The term "frac operation" as used herein may refer to fractionation of a downhole well that has already been drilled. 'Frac operation' can also be referred to and interchangeable with the terms fractionation, hydraulic fracturing, well stimulation, production enhancement, hydrofracturing, hydrofracking, fracking, fracing, and frac. A frac operation can be land or water based. Generally, the term 'fracing' or 'frac' is used herein, but meant to be inclusive to other related terms of industry art.

The phrase "processing a fluid" as used herein may refer to some kind of active step or action, such as man-made or by machine, imparted on the fluid (or fluids). For example, a fluid may be received into a device (such as a mixer) and upon processing, may leave as a 'processed fluid'. 'Processed' is not meant be limited, as this may include reference to transferred, treated, tested, measured, mixed, sensed, separated, combinations, etc. in whatever manner may be desired or applicable for embodiments herein. It is noted that while various steps or operations of any embodiment herein may be described in a sequential manner, such steps or operations may be operated in batch or continuous fashion.

The term "tracer" as used herein may refer to an identifiable substance, such as a liquid dye, liquid chemical or a particles powder, which may be followed through the course of a mechanical, chemical, or biological process. In the present disclosure, a tracer may be used in a well, and the resultant process impact on the tracer evaluated. In this respect, the tracer may help evaluate, determine, and otherwise model well production and performance. The tracer may be added (and thus may be referred to as a 'tracer additive' or 'additive') to a utility (or service, injection, etc.) fluid disposed into the well.

The term "nanoparticle" as used herein may refer to a small particle that ranges between 1 to 1000 nanometers in size diameter, and is undetectable by the human eye. A tracer in powder form may be nanoparticles. A tracer additive of the present disclosure may be in powder form with an average bulk diameter in a range of about 0.01 µm to about 10 µm.

The term "EDXRF" (Non-destructive Energy Dispersive X-Ray Fluorescence) as used herein may refer to a type of spectroscopy process (and may thus include use of a spectrometer) where a sample of material (such as a portion of produced fluid) is 'excited' in order to collect emitted fluorescence radiation, which may then be evaluated for different energies of the characteristic radiation from each of the different constituents (or elements) in the sample. The EDXRF process may be referred to as a fluorescence response-based analytical process.

EDXRF may be considered a non-destructive analytical technique used to determine the elemental composition of materials. EDXRF analyzers determine the elemental composition of a sample by measuring the fluorescent (or secondary detectable energy) X-ray emitted from a sample when it is excited by a primary X-ray source. EDXRF is designed to analyze groups of elements simultaneously to determine those elements presence in the sample and their relative concentrations—in other words, the elemental composition of the sample. Each of the elements present in a sample produces a unique set of characteristic X-rays that is a "fingerprint" for that specific element. X-rays have a very short wavelength, which corresponds to very high energy. All atoms have several electron orbitals (K shell, L shell, M shell, for example). When X-ray energy causes electrons to transfer in and out of these shell levels, X-ray fluorescence peaks with varying intensities are created and will be present in the spectrum. The peak energy identifies the element, and the peak height or intensity is indicative of its concentration.

The term "XRD" may refer to X-ray diffraction, which is a technique for analyzing the atomic or molecular structure of materials. It is non-destructive, and works most effectively with materials that are wholly, or part, crystalline. The technique is often known as x-ray powder diffraction because the material being analyzed typically is a finely ground down to a uniform state. Diffraction is when light bends slightly as it passes around the edge of an object or encounters an obstacle or aperture. The degree to which it occurs depends on the relative size of a wavelength compared to the dimensions of the obstacle or aperture it encounters.

All diffraction methods start with the emission of x-rays from a cathode tube or rotating target, which is then focused at a sample. By collecting the diffracted x-rays, the sample's structure can be analyzed. This is possible because each mineral has a unique set of d-spacings. D-spacings are the distances between planes of atoms, which cause diffraction peaks.

Referring now to FIGS. 1A, 1B, 1C, 2, and 3, together, a side view of a system for using a deployment device for the transfer of a tracer additive into a wellbore, a side view of the system with an at least partially dissolved deployment device that releases the tracer additive into the wellbore, a side view of a system for using a second deployment device for the transfer of a second tracer additive into a wellbore, a side view of a system where a remnant fluid with a tracer additive is produced from a wellbore, and a simplified block diagram of an analytical unit used to test a sample having a tracer additive according to embodiments of the disclosure, respectively, according to embodiments disclosed herein, are shown.

System 100 may include one or more components (or subcomponents) coupled with new, existing, or retrofitted equipment. System 100 may include one or more units that are skid mounted or may be a collection of skid units, and the system 100 may be suitable for onshore and offshore environments.

The system 100 may have various valves, flanges, pipes, pumps, utilities, monitors, sensors, controllers, flow meters, safety devices, etc., for accommodating sufficient universal coupling between system components and any applicable feedline/feed source of a material to be processed, any resultant product material to be discharged or transferred therefrom, and anything in between.

Figure 1B:
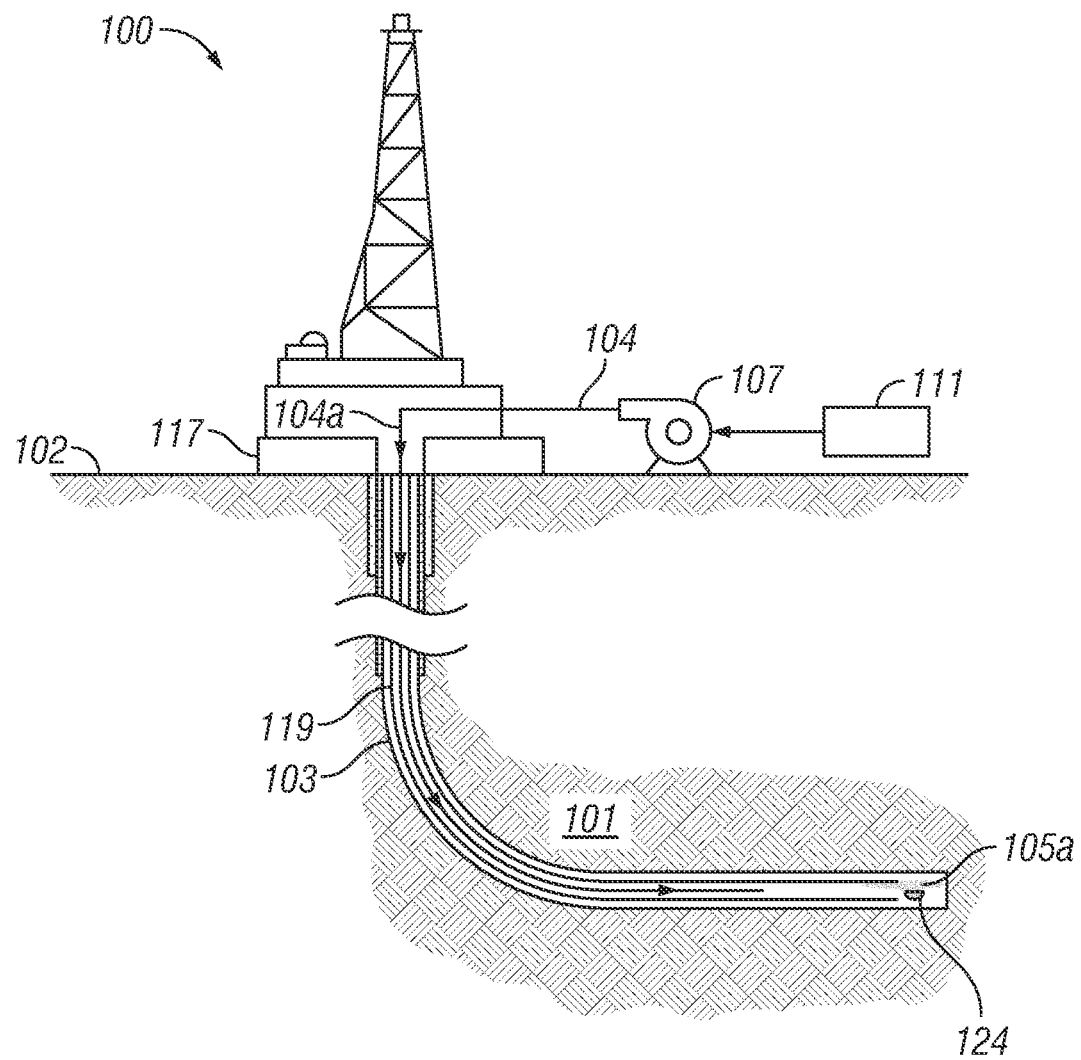
FIG. 1B shows a side view of the system of FIG. 1A with an at least partially dissolved deployment device that releases the tracer additive into the wellbore according to embodiments of the disclosure.
Figure 1C:
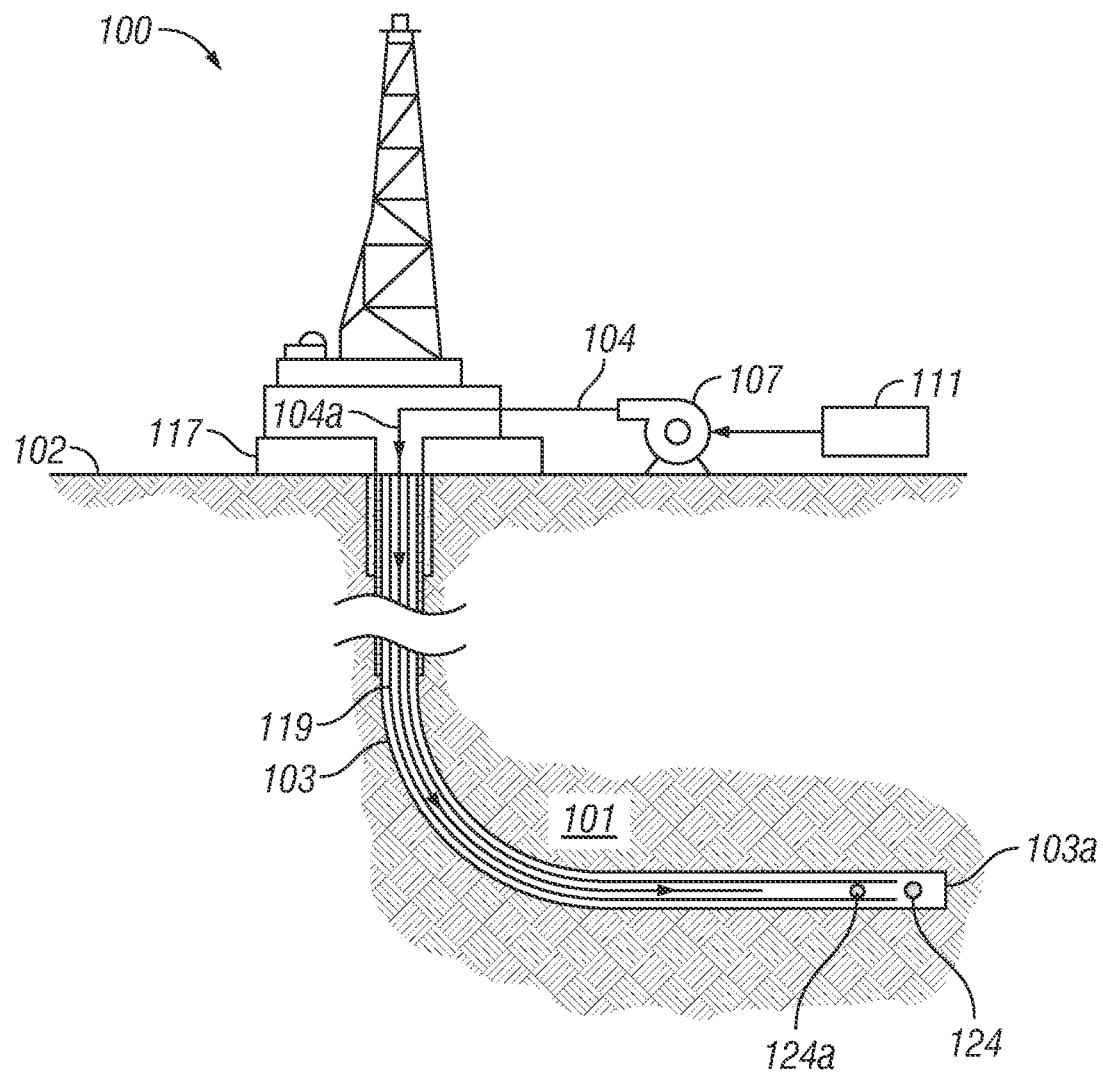
FIG. 1C shows a side view of a system for using a second deployment device for the transfer of a second tracer additive into a wellbore according to embodiments of the disclosure.

FIGS. 1A-1C are meant to show in a simplistic manner embodiments herein, and may not be to scale. The system 100 may include a subterranean or earthen formation 101 having a wellbore 103 drilled or otherwise formed therein. The formation 101 may contain hydrocarbonaceous fluids, such as oil, natural gas, and/or other materials, generally designated as F. The formation 101 may include porous and permeable rock containing liquid and/or gaseous hydrocarbons. The formation may include a conventional reservoir, an unconventional reservoir, a tight gas reservoir, and/or other types of reservoirs. Moreover, the illustration of a mover (pump) 107 is not meant to infer other equipment is not present, of which one of ordinary skill in the art is well versed. The type of mover 107 used is not meant to be limited, and other types of movers 107 may be used (even if not shown).

The system 100 may include one or more additional wellbores, production wells, etc. The example wellbore 103 shown in FIG. 1 illustrates the wellbore 103 may have at least a partial horizontal trajectory. However, any wellbore of the system 100 may include any combination of horizontal, vertical, slant, curved, directional-drilled, and/or other well geometries.

The wellbore 103 may be open, closed, cased, uncased, etc. Although not shown in detail here, the wellbore 103 may have a tubestring 119 disposed therein, such as for deploying tools or fluids into the wellbore 103. In other aspects, the tubestring 119 may be a production tubing, whereby formation and wellbore fluids may be readily transported to a surface or surface facility 102.

The formation 101 may include a target formation 101a, which may be believed to be a hydrocarbon-rich area of the formation 101. The target formation 101a may be a stage or zone, which may be part of or associated with a fracing operation. Just the same, the target formation 101a may just be part of the formation 101 without the need for enhanced oil recovery (EOR) or other type of treatment. At the end of the wellbore 103 may be the wellbore end or toe 103a.

It may be the case that the target formation 101a has perforations, which may result from a fracing operation or may naturally exist. In the event of tight formation characteristics, such as in the case of an unconventional reservoir, the target formation 101a may have an average permeability of about 0.1 nanodarcy to about 1000 nanodarcy. By way of comparison, the target formation 101a may be disposed in a conventional reservoir, and thus may have an average permeability in a range of about 0.1 millidarcy to about 1 darcy (or more).

The formation 101 might have other geologic characteristics, including hot formation temperatures. For example, the target formation 101a may have an average formation temperature T of about 450° F. In embodiments, the average formation temperature T may be in a range of about 200° F. to about 1,000° F. The formation temperature T may have a relationship to the depth, geological environment, and tightness of the formation 101.

Diagnostic information about the performance of the wellbore 103, or particular area such as by the target formation 101a, may be determined by utilizing a first tracer additive 105a. The first tracer additive 105a (or other tracer additives described herein) may be of a suitable material for use with any type of formation 101. Just the same, the first tracer additive 105a may have a (predetermined) first composition A, which results in characteristics (or traits) suitable for use in the event the formation 101 has conditions normally undesirable for the use of tracers, namely, liquid tracers.

As a first characteristic, the first tracer 105a may be a solid tracer in the form of a powder. The use of powder form makes the first tracer 105a attractive for use in high temperature conditions. The first tracer 105a may comprise powder nanoparticles. In embodiments, the particles of the first tracer 105a may have an average particle diameter of about 0.1 µm to about 10 µm. The first tracer 105a may have a first tracer specific gravity. In embodiments, the first tracer 105a may have an average bulk specific gravity of about 0.6 g/cm$^3$ to about 1.6 g/cm3. The first tracer 105a may be disposed into a first deployment device 124. Although not meant to be limited, the first deployment device 124 may be spherical in nature. The deployment device 124 may have an outer diameter. The outer diameter may be in the range of about 2 inches to about 5 inches. For example, the outer diameter may be 2.5 inches, 3.5 inches, 4.5 inches, and so forth.

Figure 5A:
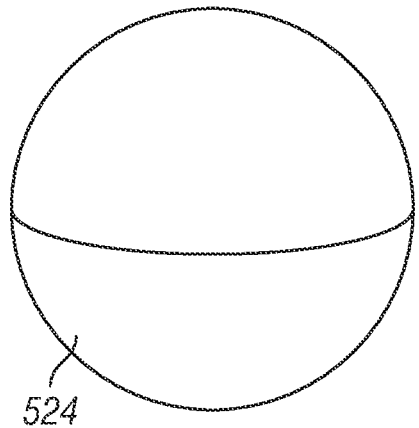
FIG. 5A shows a side view of a dissolvable deployment device according to embodiments of the disclosure.
Figure 5B:
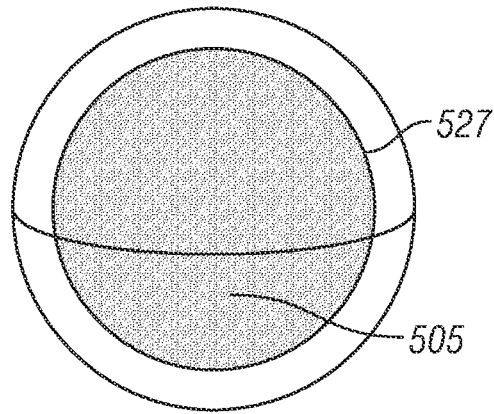
FIG. 5B shows a translucent view of the dissolvable deployment device of FIG. 5A with a tracer additive disposed therein according to embodiments of the disclosure.
Figure 5C:
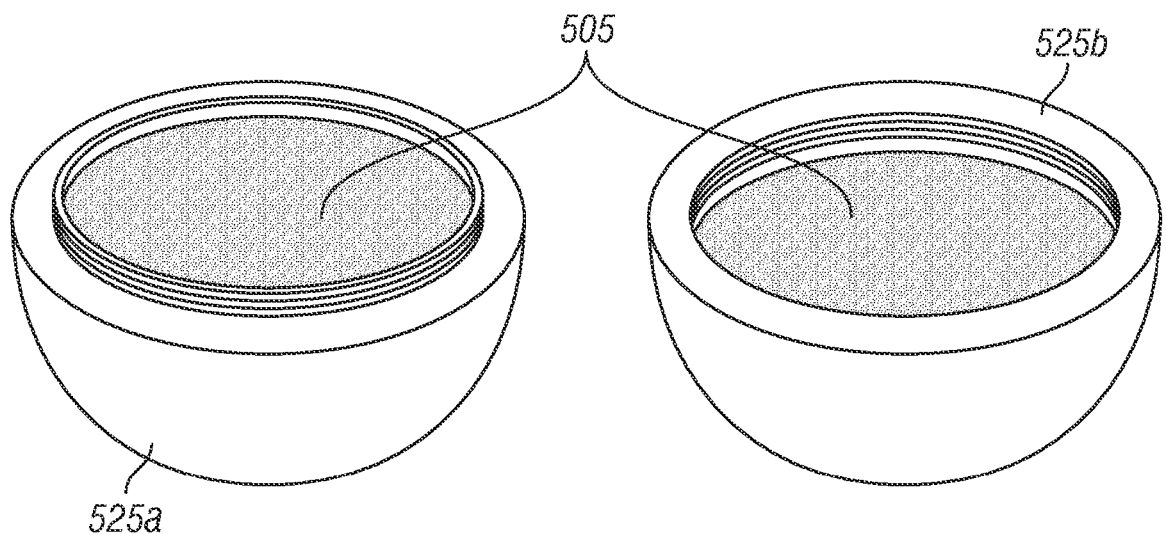
FIG. 5C shows a side view of the dissolvable deployment device of FIG. 5A separated into sections and having a tracer additive disposed therein according to embodiments of the disclosure.

Referring briefly to FIGS. 5A, 5B, and 5C, a side view of a dissolvable deployment device, a translucent view of the dissolvable deployment device with a tracer additive disposed therein, and a side view of the dissolvable deployment device of separated into sections and having a tracer additive disposed therein, respectively, according to embodiments disclosed herein, are shown.

FIGS. 5A-5C together, show the deployment device 524 may be spherical, with a (inner) hollowed region 527. The tracer additive 505 may be a solid particulate material like that of tracer additives described herein. The deployment device 524 may be separable into one or more sections 525a, 525b, etc., whereby the additive 505 may be disposed therein.

The additive 505 may be packed tightly so that as the sections 525a, 525b are coupled back together, the additive adheres or otherwise stays within the hollowed region, thus avoiding any spillage or material loss of significance. While the additive 505 could be liquidous, the use of solid material means there will not be any liquid seepage.

Figure 5D:
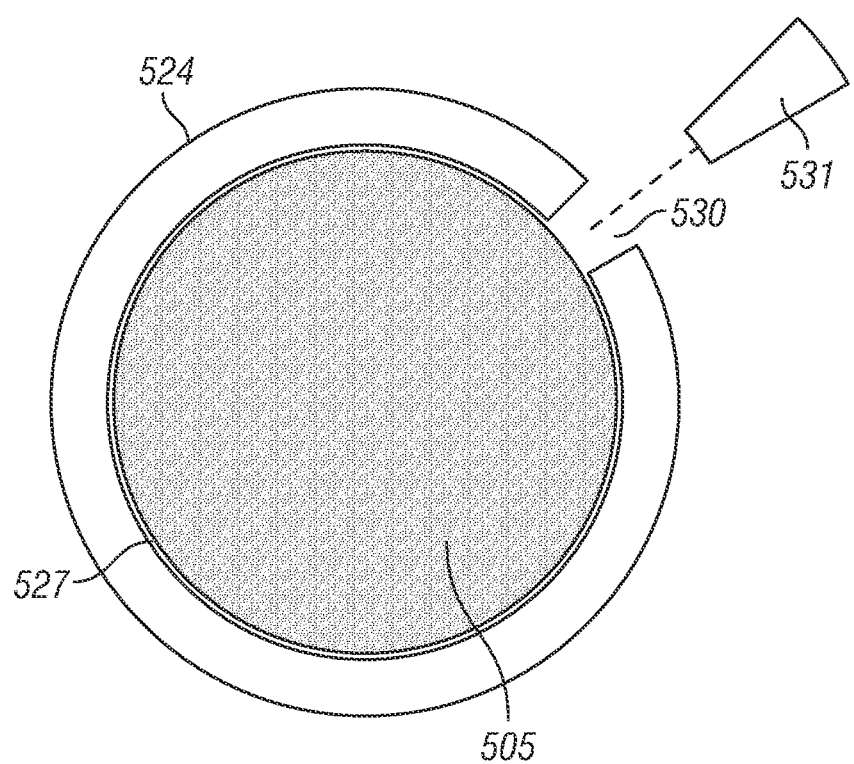
FIG. 5D shows a side view of a variant dissolvable deployment device according to embodiments of the disclosure.

In order to easily secure the sections 525a, 525b together, there may be respective mating features, such as male and female threads. However, forms of a deployment device are possible. For example, FIG. 5D shows a side view of an alternative embodiment of the deployment device 524, where there may be a removable cap or plug 531 that may securingly dispose or otherwise fit within an opening 531.

The deployment device 524 may be made of a reactive material configured to dissolve, at least partially, based on wellbore fluid composition. Reactive materials may include materials suitable for and are known to dissolve, degrade, etc. in downhole environments [including extreme pressure, temperature, fluid properties, etc.] after a brief or limited period of time (predetermined or otherwise) as may be desired). In an embodiment, a component made of a reactive material may begin to react within about 24 to about 60 hours after exposure to a reaction-inducing stimulant.

In embodiments, any deployment device of the present disclosure may be made of a metallic material, such as an aluminum-based or magnesium-based material. The metallic material may be reactive, such as dissolvable, which is to say under certain conditions the respective component(s) may begin to dissolve, and thus alleviating the need for drill thru. These conditions may be anticipated and thus predetermined. In embodiments, the components may be made of dissolvable aluminum-, magnesium-, or aluminum-magnesium-based (or alloy, complex, etc.) material.

Returning again to FIGS. 1A, 1B, 1C, 2, and 3, together, the deployment device 124 may be sent or disposed into the wellbore 103 via carrier fluid 104. For example, the pump 107 may be used to pump the carrier fluid 104 from the source 111 toward a wellhead (injection point) 117, and through the tubestring 119.

Sufficient pressure and flowrate may be selected and used in order to adequately provide the deployment device 124 to the target formation 101a. After an amount of time (which may be predetermined or otherwise known), the deployment device 124 may dissolve sufficiently enough that the first tracer 105a may begin to disperse in or at the target formation 101a. The amount of time for dispersion to begin may be about 24 hours to about 60 hours. In embodiments, the amount of time may be about 2 days.

The first tracer 105a may be completely miscible with the wellbore fluids. The first tracer 105a may be inert in the respect that there is no effect by the first tracer 105a on the carrier fluid 104 and/or the formation 101 (or target formation 101a) and/or vice versa.

The tracer 105a (or at least a portion thereof) may have an average residence time in the target formation 101a. The first tracer additive 105a may be selected for its particular uniqueness, and thus preferably has a different tracer characteristic (fingerprint) from other tracer additives used so that fluid returned to the surface may be identified. The tracer characteristic may be the chemical identity of the tracer additive used, such as composition or specific gravity. The tracer characteristic may be distinguishable from the tracer characteristic(s) of any other tracer additives used.

Figure 2:
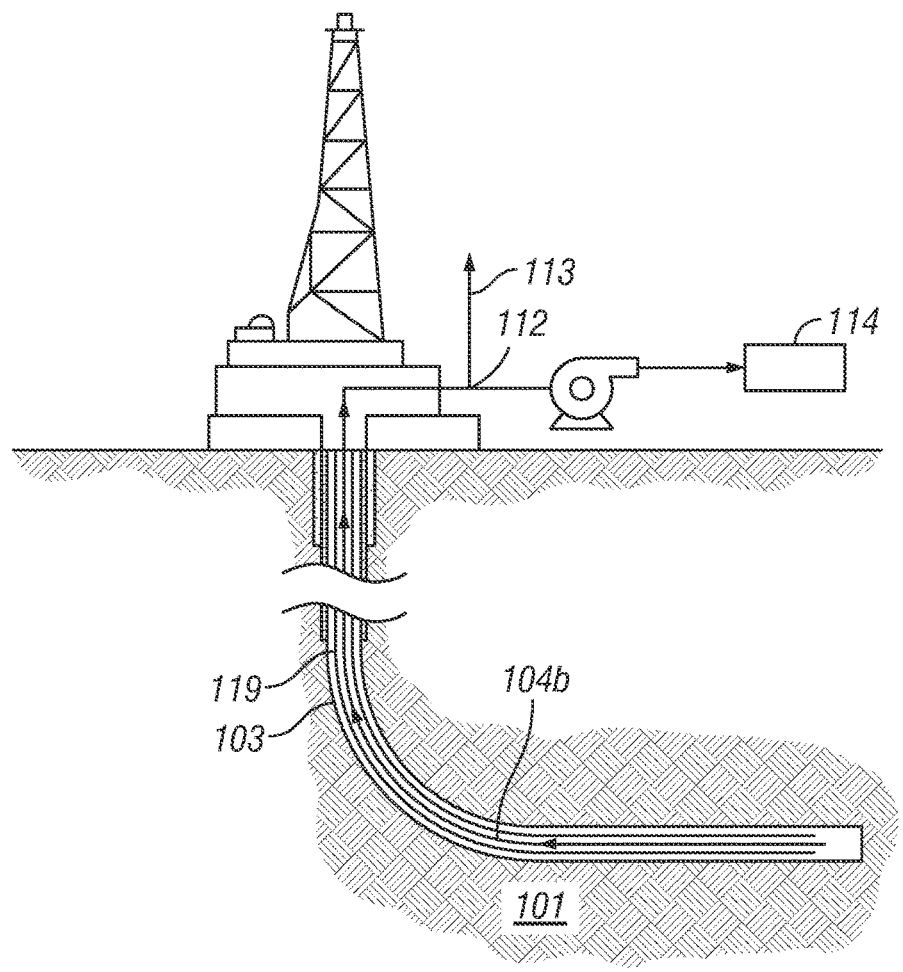
FIG. 2 is a side view of a system where a remnant fluid with a tracer additive is produced from a wellbore according to embodiments of the disclosure.
Figure 3:
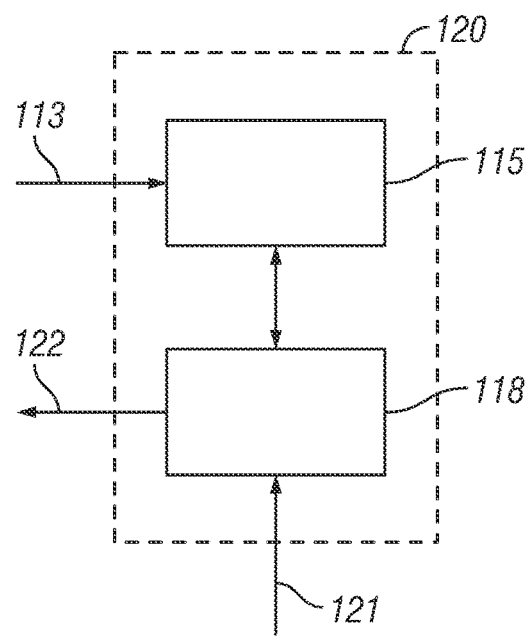
FIG. 3 is a simplified block diagram of an analytical unit used to test a sample having a tracer additive according to embodiments of the disclosure.

FIGS. 2 and 3 illustrate whereby the first tracer 105a may be brought back to the surface 102 for testing. For example, after the predetermined time period, a remnant fluid 104b may be produced. The remnant fluid 104b may include, at least partially, (some of) the first tracer 105a, the carrier fluid, and formation fluids F. A sample of the remnant fluid 104b may be produced on a desired frequency, such as daily. The sampling can occur during the desired frequency over a predetermined timeframe, which may be days or months (e.g., 6 months).

Once the remnant fluid 104b is produced from the wellbore 103, a sample 113 may be taken or extracted from sample point 112. The rest of the remnant fluid 104b may be transferred to a desired destination 114, which may be a tank, a pond, another well, or other suitable storage.

The sample 113 may now be tested via test unit 120. The test unit 120 may include analysis equipment 115, which may be in operable communication with computing system 118. The computing system 118 may be configured for use in using analytical data associated with use of the test equipment 115. The test equipment 115 may provide a fluorescence response-based process, such as EDXRF and XRD.

The computing system 118 may be useful to further analyze data and other information in order to provide an indication related to performance of the wellbore 103. This may pertain to, for example, the time the tracer additive was detected, the location where the tracer additive was use, the type and composition of the tracer additive detected, the amount or concentration of tracer additive detected, and/or other measurements provided by the equipment 115 and the system 118.

The computing system 118 may have Artificial intelligence (A.I.) based flow diagnostics. The computing system 118 may access input data 121, which may be related to other aspects of the formation 101, such as geological information, fractures, and the like. The computing system 118 may include programs, scripts, and/or other types of computer instructions that generate output data 122, which may be based on the input data 121. The output data 122 may include descriptions of fluid flow patterns in the formation 101, which may identify paths of fluid flow in the wellbore 101, wellbore breaches or cross-communication (such as to a proximate offset well), fracture locations, fluid flow rates, and/or other information.

FIG. 1C shows that a second deployment device 124a may be disposed into the wellbore 103, which may be directed to the same or different target formation. The second deployment device 124a may be disposed into the wellbore 103 in a similar manner as that of the deployment device 124. The second deployment device 124a may have a second tracer additive disposed therein (not viewable here).

The second tracer additive may be like that of the first tracer additive 105b, and thus have similar composition and characteristics; however, the second tracer additive may have a second composition B different from that of the first composition A. The use of a different composition B provides a unique identifier and fingerprint as compared to that of the composition A.

The second composition B may be different from the first composition A, yet the second tracer may have characteristics similar to that of the first tracer 105a. For example, the second tracer may be an inert solid (in powder form) having a respective average particle diameter of about 0.01 µm to about 10 μm. The second tracer may have a respective average bulk specific gravity of about 0.6 g/cm$^3$ to about 1.6 g/cm3.

As before with the first tracer 105a, after the predetermined time period, a remnant fluid 104b may be produced. The remnant fluid 104b may include, at least partially, (some of) the first tracer 105a, the second tracer, the carrier fluid, and formation fluids F.

Once the remnant fluid 104b is produced from the wellbore 103, a sample 113 may be taken or extracted from sample point 112.

The system 100 may be modified or adjusted based on the detection of tracers released from the formation 101. For example, well system tools, and/or other subsystems may be installed, adjusted, activated, terminated, or otherwise modified based on the information provided by the tracers. Additional fractures can be formed in the formation 101, and/or other modifications can be made based on information provided by the tracers. In some embodiments, modifications of the system 100 may be selected and/or parameterized to improve production from the formation 101. For example, the modifications may improve the sweep efficiency. Modifications of well system 100 may be selected and/or parameterized by the computing system based on data analysis performed by the computing system. Other or additional tracer additives and/or deployment devices may be used as desired.

Figure 4A:
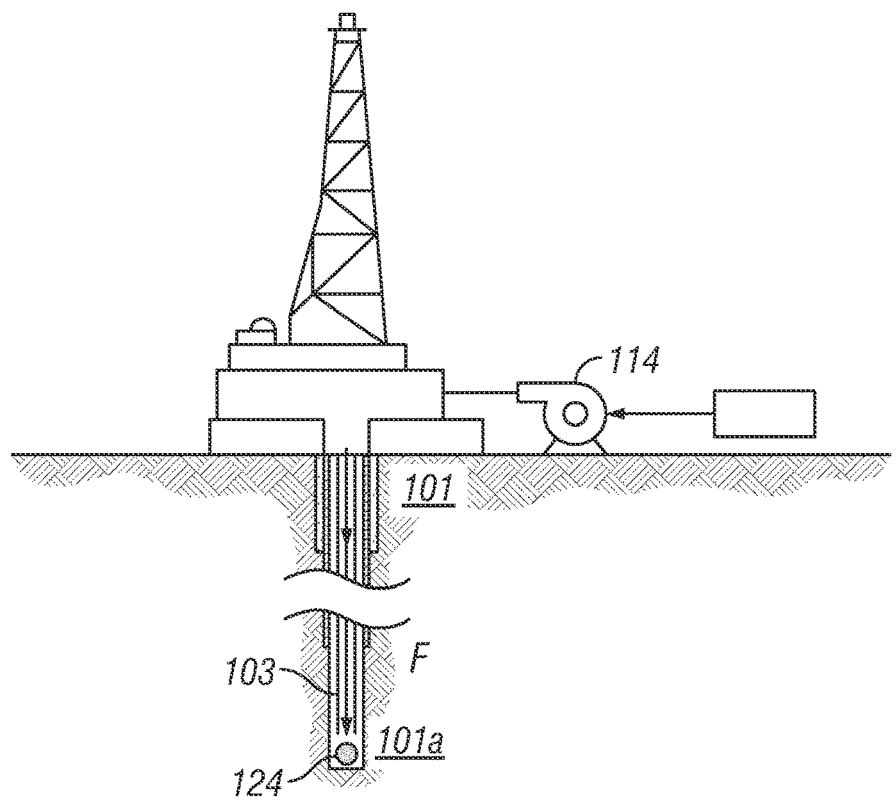
FIG. 4A shows a side view of a system for using a deployment device for the transfer of a tracer additive into a vertical wellbore according to embodiments of the disclosure.
Figure 4B:
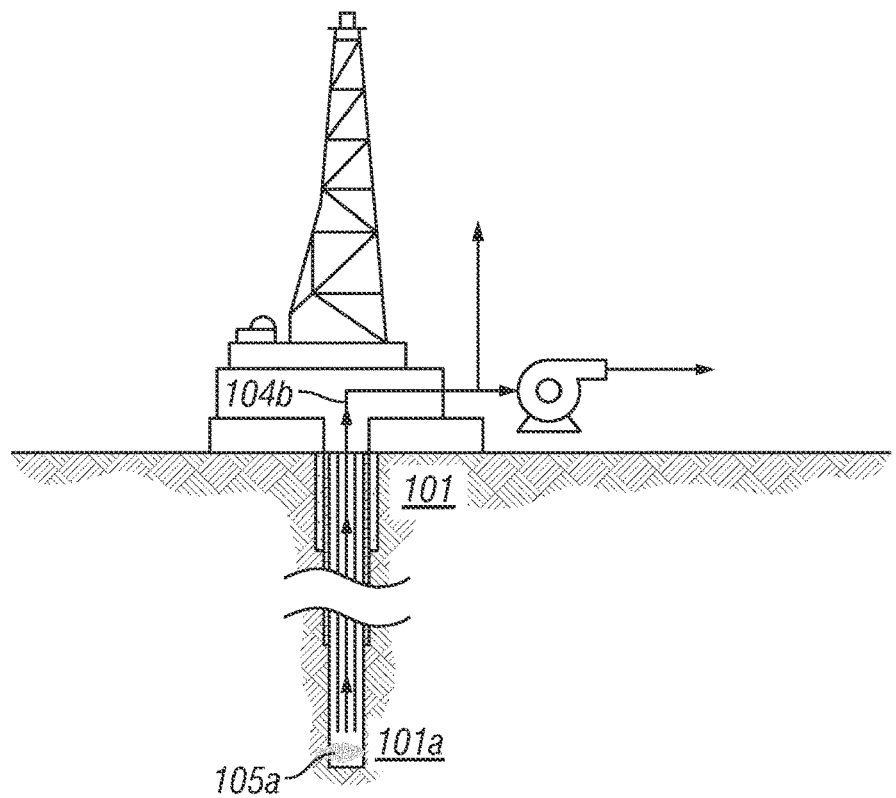
FIG. 4B shows a side view of the system of FIG. 4A with an at least partially dissolved deployment device that releases the tracer additive into the wellbore according to embodiments of the disclosure.

Referring now to FIGS. 4A and 4B together, a side view of a system for using a deployment device for the transfer of a tracer additive into a vertical wellbore, and a side view of the system with an at least partially dissolved deployment device that releases the tracer additive into the wellbore, according to embodiments disclosed herein, are shown.

FIGS. 4A and 4B show a system 100 that may be like that of other systems herein, and thus may have a formation 101 with a wellbore 103 disposed therein, which may be understood to one of ordinary skill in the art as having a vertical orientation. A carrier fluid 104a may be used to dispose a first deployment device 124 into the wellbore 103. In aspects, the deployment device 124 may be dropped, and the effect of gravity brings the deployment device to a target formation 101a, which may be the bottom of the wellbore 103. The deployment device 124 may have a first tracer additive 105a disposed therein (such as in a hollowed region (not viewable here) of the device 124). After an elapse of time, the deployment device 124 may dissolve, at least partially, in a sufficient manner whereby the first tracer additive 105a may disperse into the area proximate the target formation 101a. Then, a remnant fluid 104b (which may include at least some of the first tracer additive 105a) may be produced from the wellbore 103, which may also be tested via test unit 120 in accordance with the disclosure.

Any of the Figures herein may pertain to a geothermal well instead of a producing oil and gas well. There may still be a formation 101 with a wellbore 103 disposed therein. Instead of a hydrocarbon formation, the formation 101 may be associated with a geothermal energy-creation process. In this respect, a utility fluid having a deployment device 124 may be disposed into the wellbore 103 (or dropped via gravity feed).

Like shown in FIG. 2B or FIG. 4B, the deployment device 124 may dissolve, at least partially, such that the tracer additive 105a may disperse therefrom and come into contact with the target formation fluid. The mixing thereof may result in a remnant fluid 104b.

The geothermal properties of the formation 101 and the fluids F may result in the remnant fluid 104b having substantial thermal energy associated therewith. As such, the remnant fluid 104b may be used in an energy generation process, such as being used to create steam in order to turn a turbine. The remnant fluid 104b (e.g., a sample thereof) may also be tested via test unit 120 in accordance with the disclosure.

EXAMPLE

Embodiments herein provide for a method of using ultra-high resolution nanoparticle tracer technology. Methods of the disclosure may provide for a tracer portfolio that integrates advanced computational methods using Artificial Intelligence (A.I.). Such use may provide accurate, actionable, near real-time performance-flow-profile data. This may allow oil and gas operators to: optimize completion strategies; achieve the best production per foot; reduce completion and fracturing cost; and/or reduce environmental footprint.

Tracer technology described herein may be based on proprietary inert submicron particles and other environmentally friendly and cost-effective additives that are used to manufacture the right composition of each tracer. This tracer technology may utilize special inert particles fingerprinting with certain atoms as special indicators that enhance the properties of each tracer. These may then detected at the sub-atomic structure level using robust capabilities of EDXRF-type spectroscopy measurements, and therefore ensuring superior accuracy for each tracer's detection and characterization from different subsurface environments.

Deployed tracers are then recovered with production flowback or produced fluids from treatment or/and adjacent wells. During the back flowing of the well, reservoir oil/gas samples are taken on a regular basis, such as for the first 10 to 40 days. The number of days may as desired, such as up to 180 days. A small amount of the sample is analyzed using appropriate methods to detect the presence and concentration of tracer compound. Samples from traced and/or offset wells may be collected on a predetermined basis (such as daily) from production flowback at the wellhead or other suitable sample point. The sample may then be tested via a fluorescence response-based process, such as EDXRF and XRD. Such analytical techniques may be used to determine the elemental composition and crystallinity of the samples.

EDXRF is designed to analyze groups of elements simultaneously to determine those elements presence in the sample and their relative concentrations—in other words, the elemental composition of the sample. Each of the elements present in a sample produces a unique set of characteristic X-rays that is a "fingerprint" for that specific element. X-rays have a very short wavelength, which corresponds to very high energy.

Due to sub-atomic accuracy of both detection methods, it is possible to precisely determine the elemental composition, crystallographic structure, and the various combinations of hyperfine interactions in the samples, which enables very accurate identification of the tracer additives on the sub-atomic or quantum level.

Laboratory analysis that may include or incorporate advanced computational methods and proprietary diagnostics capabilities for each stage or target formation provides accurate, calibrated, actionable and cost-effective production diagnostics results. This enables operators to reduce operational cost and increase the production in oil and gas wells.

Embodiments herein may produce and achieve an extensive and long-term dataset from tracer additives during production flow profile analysis at each target formation. This information may be used together with advanced computational methods using Artificial Intelligence (A.I.) coupled with artificial neural network may provide precise completion optimization workflows for oil and gas wells.

Embodiments herein pertain to a method(s) of using a tracer additive in a wellbore. The method may include one or more steps, which may vary in sequence and scope. The method may include obtaining a deployment device, and disposing a tracer additive therein. The deployment device may then be disposed or otherwise transferred into the wellbore, such as via a carrier fluid.

The carrier fluid may flow at a sufficient flow rate and pressure so that the deployment device comes into contact with a target formation (in communication with the wellbore). A such, the flow rate and pressure may be adequate to transfer the deployment device through a tubestring, into the wellbore, and then into contact with the target formation.

Upon contacting or proximately locating the deployment device with the target formation for an amount of time (which may be predetermined or as otherwise desired), the deployment device may begin to, at least partially, dissolve. As such, the deployment device may be made a reactive material suitable for reacting with wellbore fluids.

Upon at least partial dissolving, the first tracer additive may disperse into the wellbore. The method may include at some point later returning (producing, etc.) a remnant fluid to a surface. One of skill would appreciate the surface refers to above-ground production equipment, facilities, and so forth, being common in production operations.

The method may include taking a sample of the remnant fluid, and then testing the sample in order to analyze the remnant fluid in order to provide a set of fluid data. The method may include integrating (or otherwise analyzing, comparing, etc.) the set of fluid data with other wellbore data in order to determine a parameter associated with performance of the wellbore.

The method may utilize the tracer additive having a first tracer composition. The tracer additive may be in powder (i.e., solid) form having an average particle diameter of at least 0.01 μm to no more than 10 μm. The tracer additive may have an average bulk specific gravity. For example, the average bulk specific gravity may be in a range of at least 0.6 g/cm$^3$ to no more than 1.6 g/cm3.

The method may include additional steps, such as disposing a second deployment device that may have a second tracer additive disposed therein into the wellbore. The disposing step may be done in such a manner that the second deployment device may come into contact with one or more of the target formation, another target formation proximate to the wellbore, or combinations thereof.

The second tracer additive may have a different composition from the first chemical tracer, but otherwise may also be in powder form, may have an average particle diameter of at least 0.1 μm to no more than 10 μm, and may have average bulk specific gravity of at least 0.6 g/cm$^3$ to no more than 1.6 g/cm3.

The testing the sample step may include using a fluorescence response-based analysis. In aspects, the fluorescence response-based analysis may include use of EDXRF. In aspects, the fluorescence response-based analysis many include use of XDR.

Embodiments herein may be used in manner that is decoupled from the use of a fracturing operation. As such, any deployment device of the disclosure may be used in a wellbore (and respective tubestring) that does not have a fluid isolation device (e.g., frac plug, bridge plug, etc.) disposed therein.

Advantages

Embodiments herein may provide for a new and improved method and system related to the use of tracers in various settings associated with an earthen formation, such as an oil and gas well.

The tracer may be cost-effective and inert, stable at (excessively) high temperatures, compatible with formation fluids, non-intrusive to completion design, easy to use, and quickly tested. Other advantages may include use of tracers that are of a cost-effective material, inert and lightweight, easily deployed, non-hazardous and non-radioactive, a single tracer for water and oil phases, and precise sub-atomic accuracy.

The tracer may be deployed via a transportation or deployment device, which may be made of a reactive material that dissolves over a period of time. Thus, the tracer is not directly mixed into a pump-down stream; instead, the tracer deploys once the transportation device sufficiently dissolves in order to release the tracer.

While embodiments of the disclosure have been shown and described, modifications thereof may be made by one skilled in the art without departing from the spirit and teachings of the disclosure. The embodiments described herein are exemplary only and are not intended to be limiting. Many variations and modifications of the embodiments disclosed herein are possible and are within the scope of the disclosure. Where numerical ranges or limitations are expressly stated, such express ranges or limitations should be understood to include iterative ranges or limitations of like magnitude falling within the expressly stated ranges or limitations. The use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the preferred embodiments of the present disclosure. The inclusion or discussion of a reference is not an admission that it is prior art to the present disclosure, especially any reference that may have a publication date after the priority date of this application. The disclosures of all patents, patent applications, and publications cited herein are hereby incorporated by reference, to the extent they provide background knowledge; or exemplary, procedural or other details supplementary to those set forth herein.

What is claimed is:

1. A method of using a tracer additive in a wellbore, the method comprising:
using a spherical deployment device, the spherical deployment device configured with a first section and a second section engageable together to form a hollowed region therein;

disposing the tracer additive in solid powder form into the spherical deployment device so that the tracer additive resides in the hollowed region upon engagement of the first section and the second section;

sending the spherical deployment device into the wellbore in manner whereby the spherical deployment device arrives at a target formation in communication with the wellbore, whereby the tracer additive in the hollowed region is initially isolated from contacting the target formation;

waiting for at least partial dissolving of the spherical deployment device so that the tracer additive comes into contact with a target formation fluid; and upon contacting the target formation fluid with the tracer additive for an amount of time, returning a remnant fluid that includes at least a portion of the tracer additive to a surface;

taking a sample of the remnant fluid;

providing the sample to a surface facility; and testing the sample at the surface facility via non-destructive energy dispersive x-ray fluorescence (EDXRF) in order to analyze the remnant fluid via energy excitation at a sub-atomic level in order to provide a set of fluid data associated with an elemental composition of the remnant fluid.

2. The method of using the tracer additive of claim 1, wherein the wellbore is associated with a formation temperature of at least 200° F. to no more than 1,000° F.

3. The method of using the tracer additive of claim 1, the method further comprising:

integrating the set of fluid data with other wellbore data in order to determine a parameter associated with performance of the wellbore.

4. The method of using the tracer additive of claim 1, wherein the deployment device has an outer diameter in a ball size range of at least 2 inches to no more than 5 inches.

5. The method of using the tracer additive of claim 1, wherein an amount of elapsed time to accomplish at least partially dissolving the spherical deployment device is in a range of at least 36 hours to no more than 240 hours, and wherein the spherical deployment device is neither a frac plug, nor a part of frac plug.

6. The method of using the tracer additive of claim 1, wherein the wellbore is a vertical wellbore, and wherein the sending the spherical deployment device into the wellbore step does not use pump down nor via connection to a workstring.

7. The method of using the tracer additive of claim 1, wherein the wellbore comprises a horizontal wellbore section, and wherein the sending the spherical deployment device into the wellbore step uses pump down but the spherical deployment device is not connected with a workstring.

8. The method of using the tracer additive of claim 1, wherein the target formation has an average permeability of 0.1 nanodarcy to 1000 nanodarcy.

9. The method of using the tracer additive of claim 1, the method further comprising sending a second deployment device carrying a second tracer additive into the wellbore so that upon dissolving of the second deployment device, the second tracer additive comes into contact with one or more of the target formation, another target formation proximate to the wellbore, a respective target formation fluid, or combinations thereof.

10. The method of using the tracer additive of claim 9, wherein the second tracer additive is a different composition from the tracer additive, but is otherwise also in powder form.

11. The method of using the tracer additive of claim 1, wherein the spherical deployment device is neither a frac plug, nor a part of frac plug.

12. The method of using the tracer additive of claim 11, wherein at no point is the spherical deployment device connected with a workstring.

13. A method of using a tracer additive in a wellbore, the method comprising:

using a deployment device, the deployment device configured with a first section and a second section engageable together to form a hollowed region therein;

disposing the tracer additive in solid powder form into the deployment device so that the tracer additive resides in the hollowed region upon engagement of the first section and the second section;

sending the deployment device into the wellbore in manner whereby the deployment device arrives at a target formation in communication with the wellbore, whereby the tracer additive in the hollowed region is initially isolated from contacting the target formation;

waiting for at least partial dissolving of the deployment device so that the tracer additive comes into contact with a target formation fluid;

taking a sample of the remnant fluid;

providing the sample to a surface facility; and testing the sample at the surface facility order to analyze the remnant fluid to provide a set of fluid data associated with an elemental composition of the remnant fluid, wherein the deployment device is neither a frac plug, nor a part of frac plug, and wherein the tracer additive is in a solid powder and has a first tracer composition.

14. The method of claim 13, wherein the tracer additive is characterized as having an average particle diameter of at least 0.01 μm to no more than 10 μm.

15. The method of using the tracer additive of claim 14, the method further comprising:

integrating the set of fluid data with other wellbore data in order to determine a parameter associated with performance of the wellbore.

16. The method of using the tracer additive of claim 15, the method further comprising sending a second deployment device carrying a second tracer additive into the wellbore, wherein the second tracer additive is initially isolated from contacting the target formation, wherein the second tracer additive is a different composition from the tracer additive, but is otherwise also in powder form.

17. The method of using the tracer additive of claim 15, wherein during the sending the deployment device into the wellbore step the deployment device is not connected with a workstring.

18. A method of using a tracer additive in a wellbore, the method comprising:

using a spherical deployment device, the spherical deployment device being made of a reactive material and configured with a hollowed region;

disposing the tracer additive into the hollowed region;

sending the spherical deployment device into the wellbore in manner whereby the spherical deployment device arrives at a target formation in communication with the wellbore, whereby the tracer additive in the hollowed region is initially isolated from contacting the target formation;

waiting for at least partial dissolving of the deployment device so that the tracer additive comes into contact with a target formation fluid; and upon contacting the target formation fluid for an amount of time, returning a remnant fluid that includes at least a portion of the tracer additive to a surface;

taking a sample of the remnant fluid; and testing the sample at the surface facility via non-destructive energy dispersive x-ray fluorescence (EDXRF) in order to analyze the remnant fluid via energy excitation at a sub-atomic level in order to provide a set of fluid data associated with an elemental composition of the remnant fluid.

19. The method of claim 18, wherein the tracer additive is in a solid powder form having an average particle diameter of at least 0.01 µm to no more than 10 µm, and wherein the spherical deployment device is neither a frac plug, nor a part of frac plug.

20. The method of using the tracer additive of claim 19, wherein during the sending the spherical deployment device into the wellbore step the spherical deployment device is not connected with a workstring.

* * * * *